United States Patent [19]

Samuelsson et al.

[11] Patent Number: 4,560,514

[45] Date of Patent: Dec. 24, 1985

[54] INFLAMMATORY LIPOXIN A AND ANTI-ANFLAMMATORY LIPOXIN B COMPOUNDS

[76] Inventors: Bengt Samuelsson, Framnåsvagen 6, 18263 Djursholm, Sweden; Charles Serhan, 2972 Waverly Ave., Oceanside, N.Y. 11572; Mats Hamberg, Antilopvägen 6, 18143 Lidingö, Sweden

[21] Appl. No.: 607,350

[22] Filed: May 4, 1984

[51] Int. Cl.$^4$ .................. C11C 1/00; C09F 5/08; C09F 7/00
[52] U.S. Cl. .................. 260/410; 260/404; 260/413
[58] Field of Search .......... 260/413 L, 410 R, 404

[56] References Cited

U.S. PATENT DOCUMENTS

| | | | |
|---|---|---|---|
| 3,862,972 | 1/1975 | Heslinga et al. | 260/413 L |
| 3,952,035 | 4/1976 | Galantay et al. | 260/413 L |

OTHER PUBLICATIONS

Samuelsson, B., Science 220:568–565, (1983).
Weissman, G. et al., N. Engl. J. Med. 303:27–34, (1980).
Serhan, C. N., J. Immunol. 125:2020–2024, (1980).
Lewis, R. A. et al., J. Exp. Med. 154:1243–1248, (1982).
Serhan, C. N. et al., Biochem. Biophys. Res. Comm. 107:1006–1012. (1982).
Lundberg, U. et al., FEBS Lett. 126:127–132, (1981).
Jubiz, W. et al., Biochem. Biophys. Res. Commun. 99:976–986, (1981).
Radmark, O. et al., In: Advances in Prostaglandin, Thromboxane & Leukotriene Research, vol. 11, pp. 61–70, Raven Press, (NY), 1982.
Maas, R. L. et al., Proc. Natl. Acad. Sci. 78:5523–5527, (1981).
Lagarde, M. et al., Biochem. Biophys. Res. Commun. 99:1398–1402, (1981).
Vanderhoek, J. Y. et al., J. Biol. Chem. 255:5996–5998 and 10064–10066, (1980).
Maas, R. L. et al., Proc. Natl. Acad. Sci. 80:2884–2888, (1983).
Sok, D–E et al., Biochem. Biophys. Res. Commun. 104:1363–1370, (1981).
Sok, D–E et al., Biochem. Biophys. Res. Commun. 110:273–279, (1983).
Turk, J. et al., J. Biol. Chem. 257:7068–7076, (1982).
Turk, J. et al., Biochim. Biophys. Acta 750:78–90, (1983).
Turk, J. et al., Advances in Prostaglandin, Thromboxane & Leukotriene Research, vol. 11, pp. 123–132, Raven Press, (1983).
Maas, R. L. et al., J. Biol. Chem. 257:7056–7067, (1982).
Maas, R. L. et al., Leukotrienes and other Lypoxygenase Products, Raven Press, NY, (1982), pp. 29–44.
Serhan, C. N., Biochem. Biophys. Res. Commun. 118:943–949, (1984).

*Primary Examiner*—J. E. Evans
*Attorney, Agent, or Firm*—Robert A. Armitage

[57] ABSTRACT

The present invention provides novel lipoxins A and B and a method of stimulating with lipoxin A compounds and attenuating with lipoxin B compounds the activation of neutrophils by exposure to an effective concentration of lipoxins or a derivative thereof. Also provided in the present disclosure are methods and compositions for preventing or treating inflammation, inflammatory responses, or inflammatory diseases and conditions in mammals, including humans, by administration of lipoxin B compounds. Lipoxins are novel trihydroxytetraene derivatives of arachadonic acid related to the leukotrienes.

3 Claims, No Drawings

INFLAMMATORY LIPOXIN A AND ANTI-ANFLAMMATORY LIPOXIN B COMPOUNDS

BACKGROUND OF THE INVENTION

The present invention relates to novel chemical compounds, pharmacological uses and compositions therefor. Particularly, the present novel invention relates to lipoxin A or 5,6,15L-trihydroxy-7,9,11,13-eicosatetraenoic acid and lipoxin B or 5D,14,15-trihydroxy-6,8,10,12-eicosatetraenoic acid and derivatives thereof and uses therefor.

Arachidonic acid plays a central role in a complex system of biological controls wherein oxygenated derivatives of a arachidonic acid, such as prostaglandins, thromboxanes, and leukotrienes are mediators. Each of these classes of compounds are metabolites of arachidonic acid and include, for example, $PGF_2\alpha$, prostacyclin or $PGI_2$, and thromboxane $A_2$. Each of these substances are formed from arachidonic acid through prostaglandin endoperoxide precursors, i.e., $PGG_2$ and $PGH_2$, through the action of a cyclooxygenase enzyme on the arachidonic acid substrate.

In contrast to the cyclopentane-containing prostaglandins and thromboxanes, the leukotrienes are acyclic arachidonic acid metabolites which are formed by transformation of arachidonic acid into an unstable epoxide intermediate, leukotriene $A_4$, which can be converted enzymatically by hydration to leukotriene $B_4$ and by addition of glutathione to leukotriene $C_4$. Leukotriene $C_4$ is metabolized to leukotriene $D_4$ and leukotriene $E_4$ by successive elimination of a gamma-glutamyl residue and glycine.

The aforementioned leukotrienes are known in the art as mediators of immediate hypersensitivity reactions and inflammation. In particular, the slow-reacting substance of anaphylaxis (SRS-A) consists of leukotrienes $C_4$, $D_4$ and $E_4$. The cysteinyl-containing leukotrienes are also potent bronchoconstrictors, increase vascular permeability in post-capillary venules, and stimulate mucus secretion. Leukotriene $B_4$ causes adhesion and chemotactic movement of leukocytes and stimulates aggregation, enzyme release, and the generation of superoxide in neutrophils. Leukotriene $C_4$, $D_4$ and $E_4$, which are released from the lung tissue of asthmatic subjects exposed to specific allergens, play a pathophysiological role in immediate hypersensitivity reactions. As such, these leukotrienes, as well as leukotriene $B_4$, have marked pro-inflammatory effects.

The first series of leukotrienes were discovered from products, e.g., 5-hydroperoxyeicosatetraenoic acid (5-HPETE), derived enzymatically from arachidonic acid through the action of a 5-lypoxygenase enzyme. For discussion of the various leukotriene metabolites of 5-HPETE, their formation and biological effects, see Bengt Samuelsson, "Leukotrienes: Mediators of immediate hypersensitivity reactions in inflammation," Science 220:568-575 (1983).

These originally discovered leukotrienes were all characterized by the initial introduction of an oxygen atom at the C-5 position. However, other enzymatic pathways were subsequently identified wherein lipoxygenase enzymes catalyze the introduction of oxygen atom at other positions besides C-5. Particularly known are leukotrienes formed with initial oxygenation at either C-12 or C-15 through 12- or 15-lipoxygenases. For example, a 15-lipoxygenase converts arachidonic acid to 15-hydroperoxy-eicosatetraenoic acid (15-HPETE). This compound is then further metabolized to 14,15-dihydroxy-5,8,10,12-eicosatetraenoic acid (14,15-diHETE) as well as 8,15-dihydroxy-5-cis-9,11,13-trans-eicosatetraenoic acids.

The present disclosure provides a new series of oxygenated derivatives of arachidonic acid which arise through interactions of multiple distinct lipoxygenase pathways and therefore are given the name "lipoxins", or LX compounds. These novel lipoxins are, like the leukotrienes, oxygenated derivatives of arachidonic acid. They contain, however, a trihydroxy-tetraene structure instead of the characteristic triene structure of the leukotrienes.

Neutrophils are leukocytes which mediate inflammatory processes in mammals. They aggregate, degranulate, generate active oxygen species, and release oxidation products of arachidonate when exposed to appropriate stimuli (See G. Weissman et al. (1980) N. Engl. J. Med. 303:27-34 and C. W. Serhan et al. (1980) J. Immunol. 125:2020-2024). Upon activation, human neutrophils release arachidonic acid from membrane phospholipids which may be oxygenated by either cyclooxygenase (prostaglandins, prostacyclin, or thromboxane) or lipoxygenase (leukotriene) pathways. For example, activation of the 5-lipoxygenase pathway leads to the formation of $LTB_4$ and its isomers, as indicated above. The fact that $LTB_4$ is a potent chemo-attractant and is the agent which stimulates secretion in human neutrophils (See R. A. Lewis et al. (1981) J. Exp. Med. 154:1243-1248 and C. N. Serhan et al. (1982) Biochem. Biophys. Res. Commun. 107:1006-1012) indicates that activation of the 5-lipoxygenase pathway plays a key role in the inflammatory response in mammals.

In addition to pro-inflammatory effects associated with the 5-lipoxygenase pathway, human leukocytes are also capable of oxygenating arachidonate by means of the 15-lipoxygenase pathway as indicated above. See U. Lundberg et al. (1981) FEBS Lett. 126:127-132; W. Jubiz et al. (1981) Biochem. Biophys. Res. Commun. 99:976-986; and O. Radmark et al. (1982) In: Advances in Prostaglandin, Thromboxane and Leukotriene Research (eds. B. Samuelsson, P. Ramwell and R. Paoletti), vol. 11, Raven Press, N.Y., pp. 61-70. Initial oxygenation at C-15 leads to the formation of 15-hydroperoxyeicosatetraenoic acid (15-HPETE) which may be further transformed to 14,15- or 8,15-hydroperoxyeicosatetraenoic acids, as indicated above. See U. Lundberg et al. (1981) FEBS Lett. 126:127-132; W. Jubiz et al. (1981) Biochem. Biophys. Res. Commun. 99:976-986; O. Radmark et al. (1982) In: Advances in Prostaglandin, Thromboxane and Leukotriene Research (eds. B. Samuelsson, P. Ramwell and R. Paoletti), vol. 11, Raven Press, N.Y., pp. 61-70; and R. L. Maas et al. (1981) Proc. Natl. Acad. Sci. 78:5523-5527. A biological role for the 15-lipoxygenase pathway and its metabolites has not heretofore been elucidated. Recent studies indicate that 15-HPETE inhibits the release of arachidonate from platelets (see M. Lagarde et al. (1981) Biochem. Biophys. Res. Commun. 99:1398-1402) and that 15-HETE, a metabolic product of 15-HPETE, inhibits not only the 12-lipoxygenase but also leukotriene biosynthesis (see J. Y. Vanderhoek et al. (1980) J. Biol. Chem. 255:5996-5998 and J. Y. Vanderhoek et al. (1980) J. Biol. Chem. 255:10064-10065).

INFORMATION DISCLOSURE

The existence of C-15 hydroxylated leukotriene-type compounds and a biochemical pathway by which arachidonic acid is converted to such compounds through a 15-lipoxygenase pathway is known. See Maas, R. L. et al., Proceedings of the National Academy of Sciences, USA, 80:2884–2888 (1983); Maas, R. L. et al., Proceedings of the National Academy of Sciences, USA, 78:5523–5527 (1981); Sok, D-E, et al., Biochemical and Biophysical Research Communications, 104:1363–1370 (1981); Sok, D-E, et al., Biochemical and Biophysical Research Communications, 110:273–279 (1983); Jubiz, W., et al., Biochemical and Biophysical Research Communications, 99:976–986 (1981); Turk, J., et al., Journal of Biological Chemistry, 257:7068–7076 (1982); Turk, J., et al., Biochimica et Biophysica Acta, 750:78–90 (1983); Turk, J., et al., "Conjugated triene metabolites of arachidonic acid derived from dioxygenation at carbon 15: Origin from eosinophil and mechanisms of biosynthesis," in: "Advances in Prostaglandin, Thromboxane and Leukotriene Research," Eds. B. Samuelsson, et al., Vol. 11, Raven Press, New York (1983); Maas, R. L., et al., Journal of Biological Chemistry, 257:7056–7067 (1982); Maas, R. L., et al., "Novel leukotrienes and lypoxygenase products from arachidonic acid" in: "Leukotrienes and Other Lypoxygenase Products," Eds. B. Samuelsson, et al., Raven Press, NY, (1982); and Radmark, O., et al., "New group of leukotrienes formed by initial oxygenation at C15" In: "Leukotrienes and other lypoxygenase products," eds. B. Samuelsson, et al., Raven Press, N.Y., (1982).

Subsequent to the making of the invention thereof herein, the existence of lipoxin A, a trihydroxy-tetraene derived from arachidonic acid, was reported by Serhan, C. N., Hamberg, M., and Samuelsson, B., Biochem. Biophys. Res. Commun., 118:943–949 (1984).

SUMMARY OF THE INVENTION

The present invention particularly provides:
(a) lipoxin A (LX-A), lipoxin B (LX-B), and derivatives thereof;
(b) a method for attenuating the activation of neutrophils in response to a stimulus which comprises:
  exposing the neutrophils to a concentration of an LX-B compound or an LX-B derivative effective to attenuate the activation of neutrophils being so exposed;
(c) a method for stimulating the activation of neutrophils in response to a stimulus which comprises:
  exposing the neutrophils to a concentration of an LX-A compound or an LX-A derivative effective to stimulate the activation of neutrophils being so exposed;
(d) a method for
  (1) preventing inflammation or an inflammatory response in a mammal susceptible to the development of an inflammation or an inflammatory response,
  (2) or treating a mammal suffering from an inflammation or inflammatory disease or condition, which comprises:
    administering to said mammal an amount of an LX-B compound or an LX-B derivative effective to prevent or treat said inflammation, an inflammatory response, or inflammatory disease or condition; and
(d) an anti-inflammatory pharmaceutical composition in a unit dosage form which comprises:
  an amount of an LX-B compound or an LX-B derivative effective to prevent or treat inflammation, an inflammatory response, or inflammatory disease or condition in a mammal to whom one or more unit doses of said composition are administered periodically in the course of a regimen of treatment.

The present invention provides the novel compounds lipoxin A or LX-A of formula XXIII (Chart A) and lipoxin B or LX-B of formula XXIV (Chart A). Chemically, lipoxin A is 5,6,15L-trihydroxy-7,9,11,13-eicosatetraenoic acid and lipoxin B is 5D,14,15-trihydroxy-6,8,10,12 eicosatetraenoic acid. Collectively, lipoxin A and lipoxin B are referred to as the "lipoxins" or "LX compounds".

In addition to encompassing LX compounds, the present invention includes LX derivatives. Specifically, the LX derivatives are derivatives of the carboxy group of an LX compound, derivatives of one of the three hydroxyl groups of an LX compound, or a bioprecursor therefor. The LX carboxyl derivatives include the pharmacologically acceptable salts of the LX compounds as well as pharmacologically useful amides and esters thereof. The LX hydroxyl group derivatives include the $C_2$–$C_8$ alkanoates, particularly the acetates.

Included within the scope of the LX derivatives are bioprecursors thereof, as the term bioprecursor is employed in U.S. Pat. No. 4,151,176, incorporated here by reference. Moreover, carboxyl derivatives of an LX compound, including salts, esters, and amides, include those customary derivatives of other eicosanoids. Refer to U.S. Pat. No. 4,112,224 incorporated here by reference, for further elaboration of such carboxyl derivatives and this manner of product from corresponding free carboxylic acids.

The present invention provides a novel method for stimulating the activation of neutrophils in mediating inflammation. Specifically the present invention provides a method by which neutrophil activation and the generation of superoxide anions are accomplished utilizing LX-A compounds and LX-A derivatives. Accordingly, the novel LX-A compounds and LX-A derivatives are useful for inducing pro-inflammatory responses and thus facilitate the study and understanding of inflammatory process and, accordingly are useful in the design and testing of anti-inflammatory properties of other pharmacologically active agents.

The present invention also provides a novel method for treating inflammation, an inflammatory response, or an inflammatory disease or condition. Particularly, the present invention provides a novel means for attenuating the activation of neutrophils in mediating inflammation. Specifically, the present invention provides a method by which neutrophil aggregation, the generation of superoxide anions by neutrophils, and the formation of pro-inflammatory leukotrienes by neutrophils through the 5-lipoxygenase pathway are inhibited by the LX-B compounds and LX-B derivatives.

The present invention further provides novel pharmaceutical compositions useful in preventing or treating inflammation. The pharmacologically active agent in these pharmaceutical compositions is an LX-B compound or an LX-B derivative. The derivatives useful in accordance with the present invention include the pharmacologically acceptable salts of the LX-B compound as well as other derivatives. These include both other derivatives of the carboxy group of the LX-B compound (e.g., esters and amides) as well as derivatives of the hydroxyl groups (e.g., $C_2$-$C_8$ alkanoates such as acetates).

The method in accordance with the present invention for attenuating the activation of neutrophils in response to a stimulus requires that the neutrophils be exposed to a sufficient concentration of an LX-B compound or LX-B derivative. In accordance with the present invention, the attenuation of neutrophil activation can result in complete inhibition of certain aspects of neutrophil activation or, alternatively, markedly reduced activation. In accordance with the present invention, the inhibition of neutrophil activation can be measured by reference to a number of end points. These include the aggregation of neutrophils, the generation of superoxide anions by neutrophils, and the formation of certain pro-inflammatory leukotrienes through the 5-lipoxygenase pathway. The method in accordance with the present invention results in the attenuation of each of these aspects of neutrophil activation.

By virtue of the effect of the LX-B compound and LX-B derivatives on neutrophils, these substances are useful for preventing or treating inflammation, inflammatory responses, or inflammatory diseases and conditions. Accordingly, this method of the present invention permits treatment of a wide variety of diseases which are characterized by inflammation mediated in whole or in part through the activation of neutrophils. Such diseases and conditions include various forms of arthritis and asthma. Also included within the present invention are those inflammatory responses to physical injury, whether through physical trauma, radiation exposure, or otherwise.

The present invention relates not only to the treatment of existing inflammatory diseases or conditions, but also to the prevention of inflammation or inflammatory response in a mammal susceptible to the development of such a condition. Such mammals include, particularly, those with asthmatic conditions who risk exposure to the antigen or antigens which precipitate an acute asthmatic attack.

Whether the method of preventing or treating inflammation in accordance with the present invention is prophylactic or therapeutic, administration of an effective amount of the LX-B compound or an LX-B derivative is required. The effective amount for administration is ordinarily that amount which is required to assure that the mammalian neutrophils involved in the inflammatory process will be exposed to a sufficient concentration of drug to inhibit their activation. Accordingly, a conventional therapeutic regimen for the administration of anti-inflammatory drugs is employed. Such a dosage regimen could consist of a single daily dosage, but would preferably employ multiple divided dosages per day. A dosage regimen can be effectively determined for each patient or animal by initial intravenous infusion at a low dosage level, e.g., 0.01 $\mu$g/kg/min and thereafter increasing the dosage until the desired effect is obtained. Thereafter, oral dosages can be determined which will yield equivalent blood levels of drug.

The methods and compositions of the present invention are preferably designed and intended to treat humans, although are similarly useful in the treatment of veterinary animals.

DESCRIPTION OF THE PREFERRED EMBODIMENTS

The operation of the present invention is more completely understood by the operation of the following examples:

EXAMPLE 1

Preparation of LX-A and LX-B as methyl esters

A. Materials

Cytochalasin B (cyto B), cytochrome C, superoxide dismutase, soybeam lipoxygenase (E.C.1.13.11.12) type I and N-tert-butoxycarbonyl-L-alanine-p-nitrophenyl ester (N-t-BOC-L-ala-PNP) are obtained, e.g. from Sigma (St. Louis, Mo.). 15-HPETE is then obtained by incubaion of arachidonic acid (Nu-Chek Prep.; Elysian, Minn.) with soybean lipoxygenase according to the procedure of Hamberg, M., et al., J. Biol. Chem. 242:5329–5335 (1967). HPLC-equipment is utilized from Waters Associated (Milford, Mass.), pump 6000A, injector U6K, and LDC (Riviera Beach, Fla.), UV-detector, LDC-III. HPLC grade solvents are used in all studies.

B. Cell Preparation and Incubation Conditions

Human leukocytes obtained from peripheral blood are prepared as by Lundberg, U., et al. FEBS Lett. 126:127–132 (1981). These preparations represent a mixed population of leukocytes (neutrophils, basophils, eosinophils, etc) where the neutrophil contribution represents >90% as determined by Giemsa strain and light microscopy. Cells are washed and suspended in a buffered salt solution (138 mM $NaCl_2$, 2.7 mM KCl, 8.1 mM $Na_2PO_4$, 1.5 mM $KH_2PO_4$, 1.0 mM $MgCl_2$ and 0.6 mM $CaCl_2$, pH 7.45) at $100 \times 10^6$ cells/ml. Leukocytes (100–500 ml of $100 \times 10^6$ cells/ml) are warmed to 37° C. in a water bath with slow continuous stirring for 5 min. 15-HPETE (100 $\mu$m) and ionophore $A_{23187}$ (5 $\mu$M) are added simultaneously in ethanol (<1% final vol/vol) and the incubations continued for an additional 30 min. Incubations are stopped by addition of 2 vol methanol.

C. Extractions and purification of LX-A methyl ester and LX-B methyl ester

Procedures for ether extraction and silicic acid chromatography are undertaken as described by Borgeat, P., et al. Proc. Natl. Acad. Sci. USA 76:2148–2152 (1979). The ethyl acetate fraction from silicic acid chromatography is evaporated, dissolved in methanol, treated with diazomethane, and then subjected to thin layer chromatography. (This TLC step is essential since non-enzymatic products of 15-HPETE interfere with both the structural analysis and bioassay of the LX compounds). Then, methyl (1-hu 14C)-11,12,15-trihydroxy-5,8,13-eicosatrienoate and methyl (1-$^{14}$C)-11,14,15-trihydroxy-5,8,12-eicosatrienoate are prepared (Refer to Bryant, R., et al., Prog. Lipid Res. 20:279–281; 1981) and added to the material eluting in the ethyl acetate fractions in order to track the triene on TLC. Thin layer chromatography (TLC) is carried out using plates coated with silica gel G and ethyl acetate-2,2,4-trimethylpentane (5:1, v/v) as solvent. A Berthold Dunnschichtsscanner is used for localization of labeled material on TLC plates. The zone containing methyl esters exhibiting tetraene UV spectra (i.e. $\lambda_{max}$ 301, but not methyl (1-$^{14}$C)-11,14,15-trihydroxy-5,8,12-eicosatrienoate or methyl (1-$^{14}$C)-11,12,15-trihydroxy-5,8,13-eicosatrienoate is scraped off and the material is recovered from the silica gel by elution with methanol. The samples are extracted with diethyl ether, dried under $N_2$ and injected into a reverse phase HPLC column. The column (500×10 mn. Polygosil $C_{18}$) is eluted with methanol/water, 70:30, v/v at 3.0 ml/min. A UV detector set at 301 nm recorded the absorption of the eluate. Fractions showing a tetraene UV spectrum (FIG. 2) are collected separately and rechromatographed in the same HPLC system to obtain a mixture of the title LX-A and LX-B as methyl esters.

D. Isolation of Compounds I and II

After TLC samples of part C are recovered from the silica gel by elution with methanol followed by diethyl ether extraction, the resulting material is then subject to reverse phase HPLC (MeOH—$H_2O$, 7:3 v/v) with the UV-detector set at 301 nm. Two major components showing strong absorption at 301 nm were obtained. Material eluting in peaks I and II are collected and rechromatographed in the same HPLC system. The UV-spectrum of material eluting in peak I (herein Compound I) is methyl 5D,14,15-trihydroxy-6,8,10,12-eicostetraenonate or LX-B methyl ester. The structure of the material eluting in peak II (herein Compound II) is the methyl ester of 5,6,15L-trihydroxy-7,9,11,13-eicosatetraenoic acid or LX-A methyl ester.

EXAMPLE 2

Saponification of LX-A Methyl Ester (Methyl 5,6,15L-trihydroxy-7,9,11,13-eicosatetraenoate) to LX-A.

Samples of LX-A methyl ester (50-250 μg) obtained from several incubations according to Example 1 are dissolved in 500 μl of tetrahydrofuran and placed under a nitrogen atmosphere in a $-70°$ C. bath with a magnetic stirrbar. Lithium hydrooxide (1 m:50 μl is added and the reaction continued for 48 hrs at 4° C. Samples are extracted and subjected to reverse phase HPLC with methanol; water; acetic acid (70:30:0.01) as solvent system. The eluates are extracted with diethyl ether and concentrated to yield LX-A, 5,6,15L-trihydroxy-7,9,11,13-eicosatetraenoic acid.

EXAMPLE 3

Saponification of LX-B Methyl Ester (Methyl 5D,14,15-trihydroxy-6,8,10,12eicosatetraenoate) to LX-B.

Preparation 1: Human neutrophils for aggregation, $O_2$ generation and elastase release.

Fresh whole blood is obtained from healthy volunteers just prior to bioassay. Neutrophil suspensions are prepared by means of dextransedimentation followed by gradient-centrifugation in Lymphoprep ®. Cells are washed and suspended in a buffered salt solution (Dulbecco's PBS pH 7.45). Neutrophil aggregation is studied utilizing a standard Payton aggregometer and recorder (Craddock, P. E., et al. J. Clin. Invest. 60:260-261, 1977) and generation of superoxide anion was measured by continuous recording of the reduction of ferricytochrome C (Serhan, C. N., et al. Biochem. Biophys. Res. Commun. 107:1006-1012, 1982). Release of elastase was determined by known methods (Baici, A., et al. Biochem. Pharmacol, 38:703-708, 1981, and Serhan, C. N., et al., In: Advances in Prostaglandin, Thromboxane and Leukotriene Research [Eds. B. Samuelsson, R. Paoletti and P. Ramwell] Raven Press, New York, vol. 11, pp. 53-62) with minor modifications. After the addition of cytochalasin B (3 min. 37° C.) N-tert-butoxy-carbonyl-L-alanine-p-nitrophenyl ester (10 μm) is added to both reference and sample cuvettes in ethanol (0.1% vol/vol) and baselines are recorded at 360 nm for 60 sec before addition of LX compounds. In each experiment LX-A methyl ester and $LTB_4$ are added to cells in ethanol (final concentration <0.1% vol/vol). Appropriate solvent controls are added to reference cuvettes.

EXAMPLE 4

Human neutrophil responses to lipoxin A

A. To determine the effect of 5,6,15L-trihydroxy-7,9,11,13-eicosatetraenoic acid (lipoxin A) on neutrophil responses, superoxide anion generation, elastase release, and aggregation of neutrophils exposed to the free acid of this compound are examined. Continuous recording techniques are utilized to examine the kinetics of neutrophil responses upon addition of lipoxin A.

B. Lipoxin A ($5 \times 10^{-7}$M) induced a rapid burst in the generation of superoxide anion and stimulated the release of lysosomal elastase while at the same concentration it exerted little to no effect in provoking aggregation.

C. In dose-response studies neither lipoxin A (free acid) nor its methyl ester provoked aggregation ($10^{-6}$–$10^{-10}$ M of) of neutrophils. However, lipoxin A proved to be a potent stimulator of superoxide anion generation. At concentrations $>10^{-7}$ M lipoxin A provoked anion generation and in this respect proved to be as potent as leukotriene $B_4$. Under these conditions the synthetic chemotactic peptide f-met-leu-phe (fMLP; $10^{-7}$ M) stimulated anion generation (14.5±5.5 S.D. nmol of cytochrome C reduced/5 min (n=12) greater than either $LTB_4$ ($5 \times 10^{-7}$ M) 6.5+3.6 nmol of Cytochrome C reduced/5 min or lipoxin A ($5 \times 10^{-7}$ M) 8.1±3.7 nmole cytochrome C reduced/5 min (n=12).

Both f-Met-Leu-Phe (fMLP) and $LTB_4$ are potent stimulators of elastase release in human neutrophils. When lipoxin A is compared to the effects of these agents, lipoxin A is approximately 2 log order less potent than either fMLP or $LTB_4$.

EXAMPLE 5

LX Compositions

Pharmaceutical compositions of LX-B in unit dosage form are prepared from pharmaceutically pure compound by adding appropriate excipients which comprise the pharmaceutically acceptable carrier therefor and dividing the resulting bulk mixture into compositions of the desired unit size.

CHART A

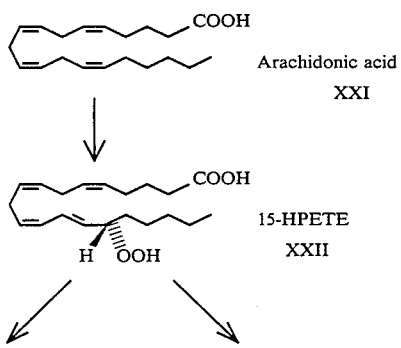

Arachidonic acid
XXI

15-HPETE
XXII

-continued

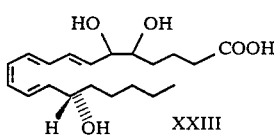
Lipoxin A (LX-A)

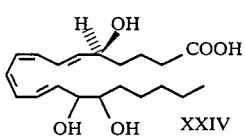
Lipoxin (LX-B)

We claim:

1. Lipoxin A, a compound of formula XXIII,

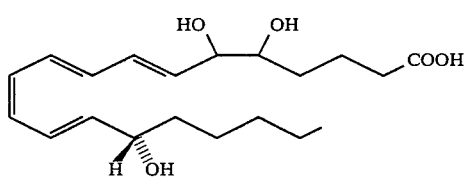

-continued
Lipoxin A (LX-A)

or Lipoxin B, a compound of formula XXIV,

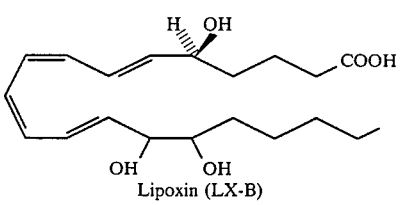
Lipoxin (LX-B)

except as Lipoxin A or Lipoxin B exist or occur in nature, or a Lipoxin A or Lipoxin B derivative of the carboxy group of the lipoxin compound or one of the three hydroxyl groups of the lipoxin compound.

2. Lipoxin A or Lipoxin A methyl ester, a compound according to claim 1.

3. Lipoxin B or Lipoxin B methyl ester, a compound according to claim 1.

* * * * *